(12) United States Patent
Yadav et al.

(10) Patent No.: US 10,426,809 B2
(45) Date of Patent: Oct. 1, 2019

(54) NANOBIOCOMPOSITE FORMULATION FOR WOUND HEALING AND A PROCESS FOR THE PREPARATION THEREOF

(71) Applicant: Council of Scientific & Industrial Research, New Delhi (IN)

(72) Inventors: Sudesh Kumar Yadav, Palampur (IN); Rubbel Singla, Palampur (IN); Avnesh Kumari, Palampur (IN)

(73) Assignee: Council of Scientific & Industrial Research, New Delhi (IN)

(*) Notice: Subject to any disclaimer, the term of this patent is extended or adjusted under 35 U.S.C. 154(b) by 0 days.

(21) Appl. No.: 16/069,672

(22) PCT Filed: Jan. 12, 2017

(86) PCT No.: PCT/IN2017/050018
§ 371 (c)(1),
(2) Date: Jul. 12, 2018

(87) PCT Pub. No.: WO2017/122224
PCT Pub. Date: Jul. 20, 2017

(65) Prior Publication Data
US 2019/0015468 A1    Jan. 17, 2019

(30) Foreign Application Priority Data
Jan. 12, 2016 (IN) .............................. 201611001043

(51) Int. Cl.

| | |
|---|---|
| *A61K 36/61* | (2006.01) |
| *A61K 9/00* | (2006.01) |
| *A61K 9/06* | (2006.01) |
| *A61L 15/28* | (2006.01) |
| *A61L 15/46* | (2006.01) |
| *A61P 17/02* | (2006.01) |
| *A61P 31/04* | (2006.01) |
| *A61K 9/51* | (2006.01) |
| *A61K 33/38* | (2006.01) |
| *A61K 47/38* | (2006.01) |
| *A61L 15/18* | (2006.01) |
| *A61L 15/44* | (2006.01) |
| *A61L 15/60* | (2006.01) |
| *A61L 15/64* | (2006.01) |

(52) U.S. Cl.
CPC ............ *A61K 36/61* (2013.01); *A61K 9/0014* (2013.01); *A61K 9/06* (2013.01); *A61K 9/5161* (2013.01); *A61K 33/38* (2013.01); *A61K 47/38* (2013.01); *A61L 15/18* (2013.01); *A61L 15/28* (2013.01); *A61L 15/44* (2013.01); *A61L 15/46* (2013.01); *A61L 15/60* (2013.01); *A61L 15/64* (2013.01); *A61P 17/02* (2018.01); *A61P 31/04* (2018.01); *A61K 2236/13* (2013.01); *A61K 2236/39* (2013.01); *A61K 2236/51* (2013.01); *A61K 2236/53* (2013.01); *A61L 2300/104* (2013.01); *A61L 2300/404* (2013.01); *A61L 2300/412* (2013.01); *A61L 2400/12* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 5,514,657 | A | 5/1996 | Shoshan et al. |
| 6,140,257 | A | 10/2000 | Kershaw et al. |
| 7,390,499 | B2 | 6/2008 | Serafica et al. |
| 7,704,523 | B2 | 4/2010 | Serafica et al. |
| 2008/0108772 | A1 | 5/2008 | Oksman et al. |
| 2010/0233245 | A1 | 9/2010 | Narayana |
| 2012/0282348 | A1 | 11/2012 | Yates et al. |
| 2013/0018112 | A1* | 1/2013 | Thielemans ......... B01J 13/0091 514/781 |
| 2013/0211308 | A1 | 8/2013 | Wan et al. |
| 2013/0330417 | A1 | 12/2013 | Dong et al. |

FOREIGN PATENT DOCUMENTS

| | | |
|---|---|---|
| CN | 104153120 A | 11/2014 |
| DE | 10342258 A1 | 4/2005 |
| EP | 2513149 B1 | 1/2016 |

OTHER PUBLICATIONS

International Search Report and Written Opinion, completed Jun. 15, 2017, pertaining to PCT/IN2017/050018, filed Jan. 12, 2017.

\* cited by examiner

*Primary Examiner* — Michael Barker
(74) *Attorney, Agent, or Firm* — Dinsmore & Shohl LLP

(57) ABSTRACT

The present invention involves the isolation of plant based CNCs from the leaves of *S. cumini*. For the formation of NCs, a novel greener approach using *S. cumini* LE as reducing agent for in situ impregnation of AgNPs as fillers into CNCs as matrix is reported. The silver nitrate solution in three different concentrations of 1 mM, 5 mM and 10 mM was used to form NCs where AgNPs have been incorporated into CNCs matrix. The CNCs and NCs were characterized using SEM, TEM, XRD, Zeta potential, FT-IR, and UV-Vis spectroscopy. NCs developed in the form of film and ointment showed strong antimicrobial activity against both gram negative and gram positive bacteria. NCs wound dressing is capable of regulating wound exudates and providing moisture to wound responsible for faster healing of acute wounds. The observations from histopathological and biochemical assays confirmed that NCs enhance healing because of lesser inflammation, rapid angiogenesis, early collagen formation and enhanced rate of reepithelization.

8 Claims, 13 Drawing Sheets

Figure 1:
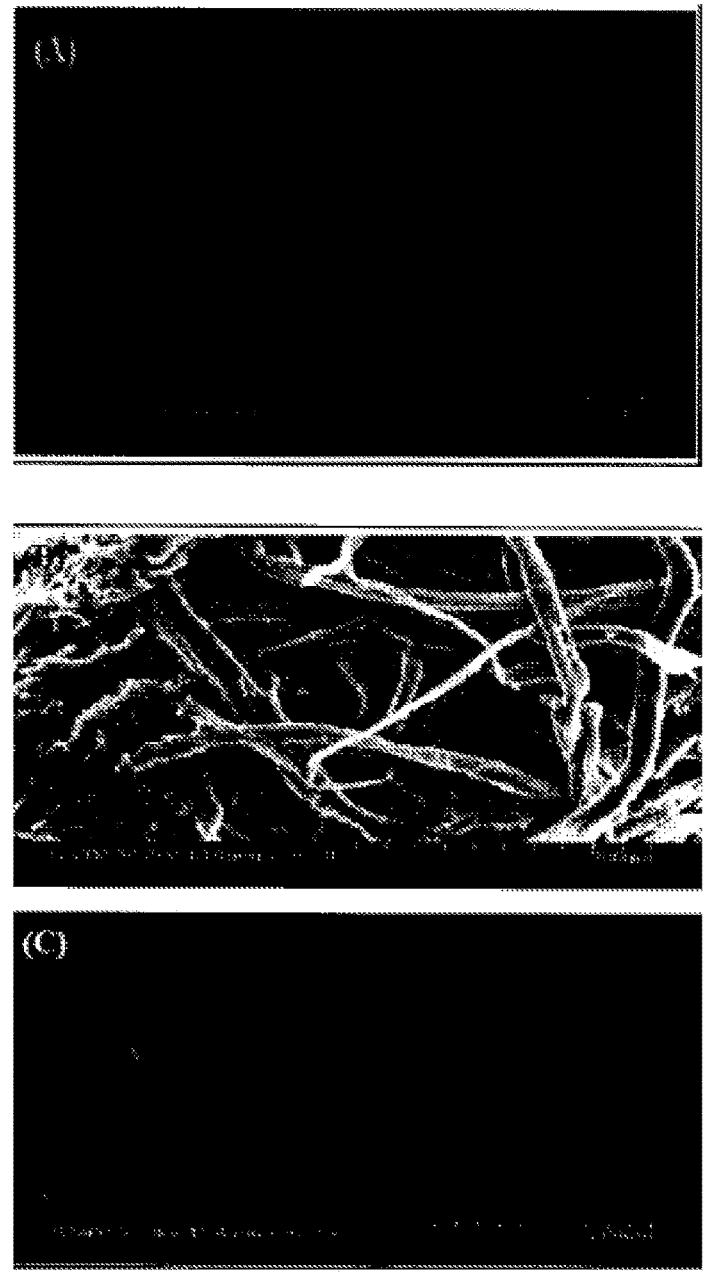

NANOBIOCOMPOSITE FORMULATION FOR WOUND HEALING AND A PROCESS FOR THE PREPARATION THEREOF

FIELD OF THE INVENTION

The present invention relates to a nanobiocomposite formulation for wound healing. Particularly, the present invention relates to a chemo-mechanical synthesis of cellulose nanocrystals (CNCs) from the biological plant material i.e. leaves of *Syzygium cumini* (Jamun) and a process for the preparation of environmental benign nanobiocomposites (NCs). Two different forms of NCs i.e. strip and ointments have been documented. More particularly, the present invention relates to the development and use of NCs of plant nanocellulose impregnated with nanosilver as antibacterial wound care products.

BACKGROUND OF THE INVENTION

The present invention envisages wound dressing comprising of plant based cellulose nanocrystals matrix incorporated with nanosilver exhibiting excellent bactericidal and wound healing effects. The invention also relates to nanobiocomposite in the form of strip/film of virtually any shape or size as well as ointment and a production process thereof.

Wound healing is a complex event consisting of joint activities of many cell and tissue lineages proceeding through various biological pathways, depends upon numerous factors which are still under investigation. Wounds have been classified into various types: open and closed wound; acute and chronic wound; incision and excision wound. Initial phase of wound healing involves blood clot formation and inflammation. Inflammation is greatly enhanced if the wound of subject becomes a target of bacterial infection. Treatment of wounds such as, but not limited to, cuts, second and third degree burns, pressure ulcers, diabetic ulcers, surgical wounds, and various skin abrasions becomes difficult because of microbial infections. As inflammation subsides, the proliferation phase starts where the fibroblasts enter the wound site leading to formation of collagen fibrils responsible for wound closure and tissue regeneration. An impaired wound healing deals with prolonged inflammation, disjunction of wound tissue edges, and excessive formation of scar tissue without restoring normal structure and function of skin. A large number of efforts had already been put forward to overcome these problems related to impaired/delayed wound healing so as to inhibit the bacterial infection, promote the growth of fibroblasts and other specialized cells to enhance the rate of re-epithelization and eventually tissue regeneration. Some studies suggested that the capacity of moisture donation and absorption of wound exudates also play a role in optimal wound healing.

An ideal dressing material is not only meant to accelerate wound healing but also reduce loss of fluid from the wound, help to minimize pain and infection, provide protection to fragile skin, and should be non-adherent to wound. A variety of wound dressing materials are available in the global market to meet the needs and provide a better life to the patient. A wide variety of materials are available for the fabrication of wound dressings whose applicability depends upon the nature of wound to be treated. U.S. Pat. No. 6,140,257 describes the use of an absorbent, composite fiber as wound dressing comprising a matrix of 10% to less than 50% water insoluble alginate having dispersed therein at least 40% of another polysaccharide. A variety of other water absorbing active ingredients used in wound care products mentioned in prior art (U.S. 20130330417 A1) are chemically modified cellulose fibers, pectin fibers, alginate fibers, collagen fibers, chitosan fibers, hyaluronic acid fibers or other polysaccharide fibers.

Silver has been known as an antiseptic for ages. Silver, copper, zinc are used in the field from a long past. Even the nanocrystalline silver has been impregnated into gauze, alginate, hydrocolloids and foams for designing wound care products. These dressings are used for treatment of a particular type of wound depending upon their advantages. Gauzes used as dressing material adhere to the wound surface causing a pain and damage to neo-epithelium during removal of gauze. Some reports describe that alginate used in wound care products may cause long term foreign body type reaction. Hydrocolloids used in wound care have not been indicated for heavily exuding wounds and produce malodor. The foams may also produce excessive malodorous drainage which necessitates the frequent change of dressing. U.S. Patent No. 20120282348 A1 reports the use of silver hydrogels for the treatment of burn wounds by receiving or donating moisture. U.S. Pat. No. 5,514,657 A mentions about the topical antibacterial application of silver sulfadiazine and collagen for wound healing especially burn wounds. In-spite of their advantages, the products are generally expensive and exhibit less exudates absorption.

A large number of synthetic and natural polymers are present in market to be used in wound healing products. Synthetic polymers such as polyurethanes, polyvinylpyrolidone (PVP), polyethyleneoxide (PEO) and polyvinyl alcohol (PVA) can be used in combination with other synthetic or natural polymers to achieve great properties optimal for healing e.g. moisture retention, re-swelling capability, and absorption of wound exudates. Natural polymers like collagen and alginates have been exploited for wound dressing. Even though these possess good water absorption/donation capacity but biocompatibility and cost are the issues related to their use.

An alternate biopolymer, cellulose also possesses inherent characteristics responsible for accelerated wound healing. It is the most abundant, oldest, biocompatible, renewable bioresource present on the earth. Cellulose has high tensile strength because of its inherent hydrogen bonding structure. Cellulose nanocrystals (CNCs) or nanofibers are developed as a new class of nano-materials having wide range of utilities as a reinforcing agent in nanocomposites, and in biomedical field. The natural sources like plants, agricultural wastes, bacteria, tunicates have been considered as raw material for cellulose. The plant sources earlier used for isolation of CNCs include wheat straw, husk, soy hulls, banana, bamboo, agricultural wastes, wood or culm of some plants. EP 2513149 A1 describes the isolation of CNCs from vegetative biomass such as flex and hemp using ammonium persulphate. U.S. Patent No. 2008/0108772 describes a process for producing cellulose nano whiskers by treating microcrystalline cellulose with HCI, as well as a new extrusion method to produce a reinforced organic polymeric material. The production of cellulose nano whiskers using HCI hydrolysis required pure cellulosic materials (e.g. MCC) and the resulting cellulose nano whiskers had a large size distribution. A number of ways are known to isolate CNCs such as chemical, mechanical, enzymatic, and chemical combined with mechanical method. Still there is a need to optimize the process parameters using an appropriate methodology to produce CNCs, free from non-cellulosic impurities having narrow size distribution so as to make use of these isolated CNCs in biomedical areas especially wound care. Cellulose fiber and cotton fibers are most suitable for surgical operations and medical treatment in view of their excellent moisture absorbency, water absorbency, and flexibility. The bacteria *Acetobacter xylinum* has also been considered to isolate cellulose. Bacterial cellulose has been reported for wound healing application due to its high water uptake capacity and purity. U.S. Pat. No. 7,704,523 B2 describes the use of microbial derived cellulose for treatment of chronic wounds. U.S. Patent No. 20130211308 A1 describes the use of nanosilver coated bacterial cellulose for wound healing due to its water uptake potential. U.S. Pat. No. 7,390,499 B2 describes the use of a mixture of cellulose and microbiocide as a wound healing agent. The chemical composition of bacterial cellulose is almost similar to plant cellulose. The problem existing with the use of microbial cellulose is that it is difficult and expensive to manufacture. The bacterial strains lose their ability to synthesize cellulose during their growth in culture and they fail to maintain their integrity during application. Furthermore, manufacturing, processing and use of microbial cellulose fail to provide a continuous source of wound dressing used in different types of wounds. Bacterial cellulose having high water retaining capacity may also enhance the chances of bacterial infection due to excessive moisture around the wound site. There is a need to put efforts to isolate plant CNCs. Plant cellulose is easy to extract, environmentally benign, abundant in nature, renewable, biocompatible, cost effective, and have good water absorption capacity.

The prior art has failed to provide a wound dressing material which have the collective potential of optimum wound healing, ability of moisture management, antimicrobial activity, anti-inflammatory activity, and adequate biocompatibility. In the present invention, attempts have been made to isolate CNCs from *Syzygium cumini* plant leaves. To solve the aforementioned problems related to wound care products, designing of nanobiocomposite containing plant CNCs and nanocrystalline silver (AgNPs) is described to meet the criteria of ideal wound dressing as it has a synergistic role of water management and antimicrobial action suitable for promotion of wound healing. The biocompatible and cost effective wound dressing of present invention in the form of thin strip and ointment assist in wound healing by decreasing the rate of inflammation, promoting proliferation and granulation, decreasing scar formation, allowing epithelial migration, early collagen formation, increasing rate of wound closure and ultimately enhancing re-epithelization. Nanosilver particles incorporated in nanocellulose have anti-microbial, anti-inflammatory action and also help to minimize scarring. AgNPs help in conversion of fibroblasts into myofibroblasts which have an impact on wound closure. In addition to this, wound dressing of present invention neither degrade nor leave any residue at the wound site. The wound dressing does not adhere to the wounded skin while removal and does not cause any pain.

OBJECTIVES OF THE INVENTION

The main object of the present invention is to provide isolate cellulose nanocrystals (CNCs) from the leaves of *Syzygium cumini* by chemo-mechanical method and their characterization.

Another object of the present invention is to provide the adoption of green approach to develop nanobiocomposites (NCs) comprising in situ impregnation of silver nanoparticles AgNPs on CNCs matrix. Preparation of thin strip/film and ointment of NCs as wound care products.

Yet another object of the present invention is to provide evaluation of developed NCs for antibacterial and in vivo acute wound healing potential.

SUMMARY OF THE INVENTION

Accordingly, the present invention relates to a nanobiocomposite formulation (NCs) comprising silver nanoparticles (AgNPs) and cellulose nanocrystals (CNCs) wherein the ratio of AgNPs and CNCs is in the range of 0.067%-0.4% w/w (AgNPs): 7-8% w/w (CNCs) in ointment form.

In an embodiment of the present invention wherein the novel product nanobiocomposite, NCs comprised of *S. cumini* isolated CNCs matrix impregnated with AgNPs synthesized using leaf extract of *S. cumini* for use as anti-bacterial acute wound healing agents.

In a preferred embodiment of the present invention provides a process for the preparation of the nanobiocomposite formulation comprising the steps:
a) treating washed and dried *Syzgium cumini* leaves with bleaching agent at pH in the range of 3.0-4.0 for a time period ranging between 2-3 h at a temperature ranging between 70–100° C. to obtain a bleached fibrous material;
b) filtering and washing the bleached fibrous material as obtained from step (a) followed by treating with acidified bleaching agent solution at a temperature ranging between 22–30° C. for a time period ranging 16-18 h to obtain acidified fibrous material;
c) washing the acidified fibrous material as obtained from step (b) followed by keeping it into each of 2-18% base for 2 to 5 h each at 70 to 80° C. under continuous stirring to obtain fibrous material;
d) treating the fibrous material from step (c) with 0.6 to 3% sodium chlorite solution for a time period ranging from 0.5 to 3 h at a temperature ranging from 80-100° C. followed by filtrating and washing to obtain a chemically treated fiber;
e) treating the chemically treated fiber as obtained from step (d) with 64-67% (v/v) acid in the ratio ranging from 1:5-1:9 for a time period ranging from 30-120 mM at a temperature ranging from 40 to 80° C. under continuous stirring to obtain acidified chemically treated fiber;
f) centrifuging and dialyzing the acidified chemically treated fiber as obtained from step (e) against water to remove the acid content until neutral to obtain cellulose nanocrystals, CNCs;
g) treating the cellulose nanocrystals, CNCs as obtained from step (f) mechanically by known methods for a time period ranging from 4-30 mM to individualize the fibers and freeze drying to obtain white solid CNCs;
h) dipping *Syzygium cumini* leaves in water for a period of time in the range of 20-28 h at a temperature in the range 20-30° C. followed by filtration and storing at a temperature 4-10° C. to obtain leaf extract as a biological reducing agent;
i) freeze drying of CNCs as obtained from step (g) and adding each of 1 mM, 5 mM and 10 mM (1-10 mM) silver nitrate solution and sonicating for 2 to 5 min to obtain a mixture;
j) adding 10-20% v/v of *Syzgium cumini* leaf extract as obtained from step (h) to each of the mixture as obtained from step (i) under continuous stirring for a time period ranging from 4 to 8 h at a temperature in the range of 20-30° C.;

k) centrifuging the mixture as obtained in step (j) to obtain nanobiocomposite, NC formulation;

In another embodiment of the present invention provides the process, wherein the bleaching agent used is selected from a group consisting of sodium chlorite, ammonium persulphate and hydroxide peroxide.

In still another embodiment of the present invention provides the process, wherein the acid used is selected from a group of sulphuric acid, nitric acid, hydrochloric acid or a mixture thereof.

In yet another embodiment of the present invention provides a process, wherein the base used is selected from a group of potassium hydroxide, sodium hydroxide.

In a preferred embodiment of the present invention provides the NC formulation is used for wound healing in the form of strip or ointment.

In another embodiment of the present invention provides the process for the preparation of the nanobiocomposite formulation, wherein the NCs pellet is directly mixed with Vaseline base in the ratio of 1:1 to obtain ointment.

In another preferred embodiment of the present invention provides the NC formulation is dissolved in water and vortexed properly to obtain aqueous suspension which is carted into a mold and allowed to oven dry in the form of NCs strip.

BRIEF DESCRIPTION OF ACCOMPANYING DRAWINGS

FIG. 1: Scanning electron microscope (SEM) image of *S. cumini* (A) untreated crushed leaf; (B) chemically pre-treated leaf fibers after bleaching treatment; (C) chemically pre-treated leaf fibers after alkali treatment.

Figure 2:
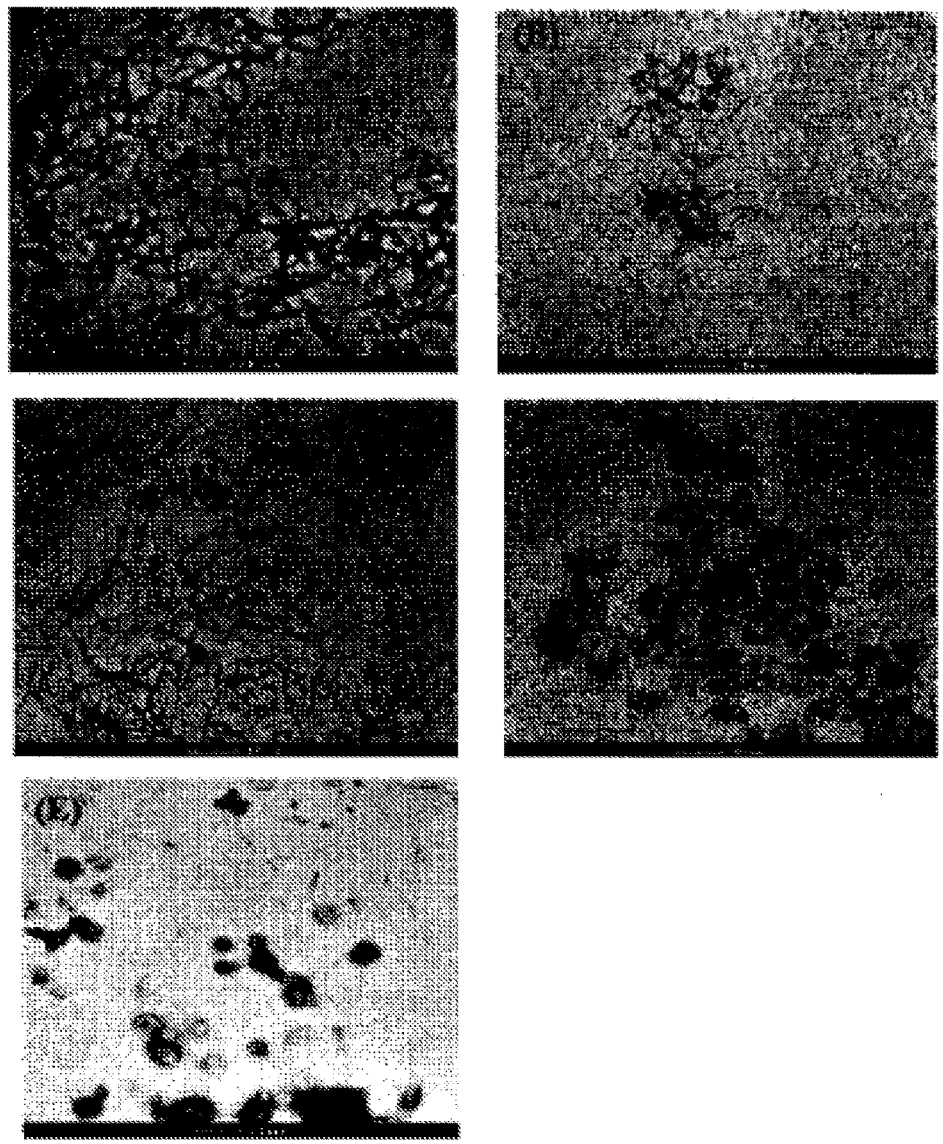

FIG. 2: Transmission electron microscopy (TEM) images of aqueous suspension of *S cumini* cellulose nanocrystals (CNCs) at (A) 4 min; (B) 8 min; (C) 12 min; (D) 20 min; and (E) 30 min of sonication.

Figure 3:
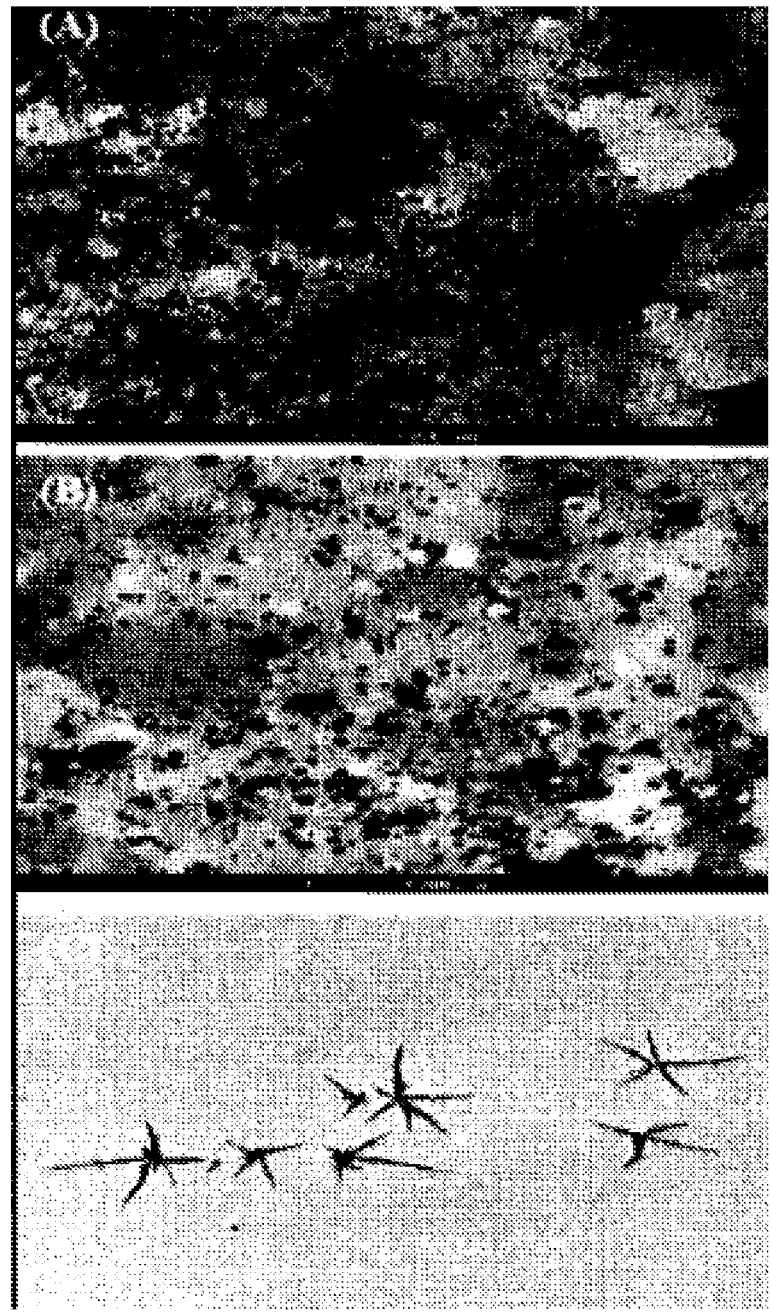

FIG. 3: Transmission electron microscopy (TEM) images of (A) nanobiocomposite formed from CNCs and 1 mM silver nitrate; (B) nanobiocomposite formed from CNCs and 5 mM silver nitrate; (C) nanobiocomposite formed from CNCs and 10 mM silver nitrate solution.

Figure 4:
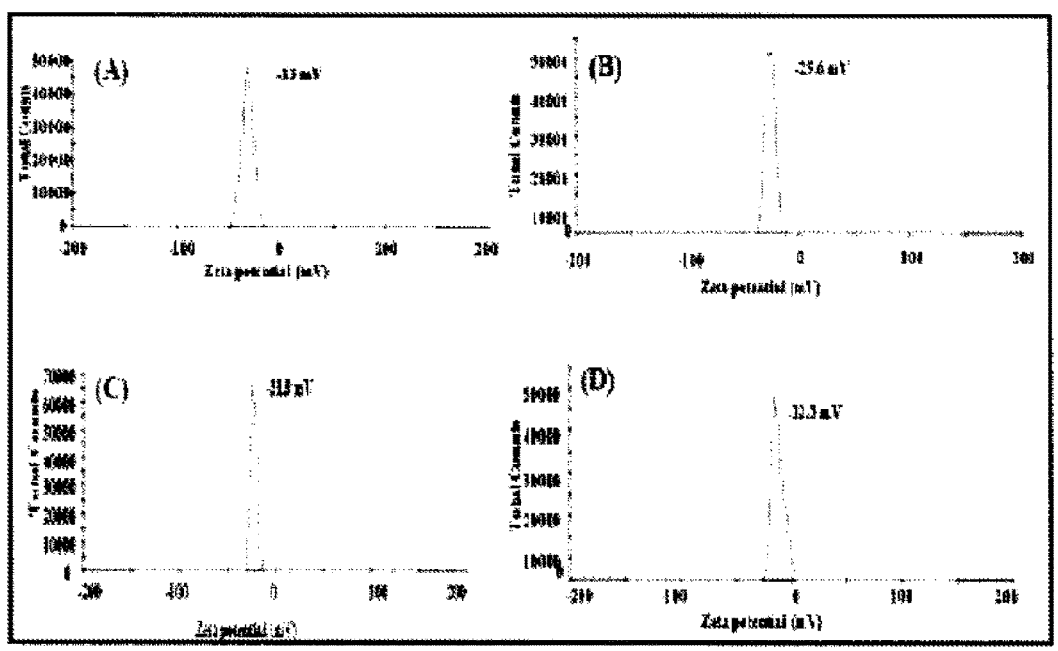

FIG. 4: Zeta potential of aqueous suspension of (A) *S. cumini* cellulose nanocrystals; (B) nanobiocomposite formed from CNCs and 1 mM silver nitrate; (C) nanobiocomposite formed from CNCs and 5 mM silver nitrate; (D) nanobiocomposite formed from CNCs and 10 mM silver nitrate solution.

Figure 5:
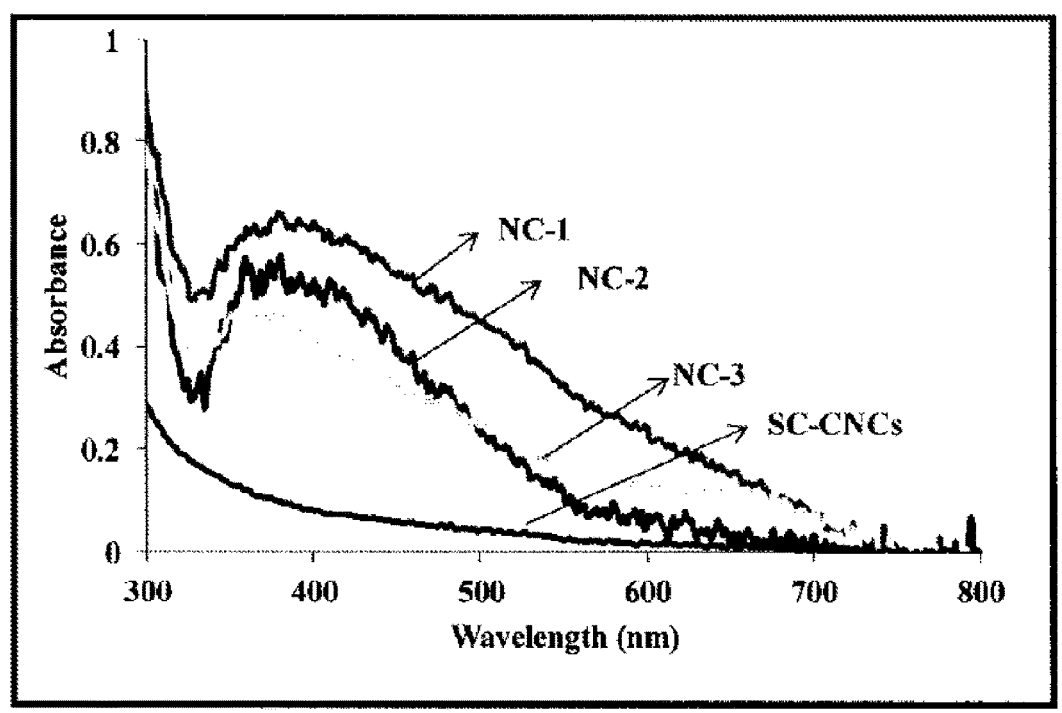

FIG. 5: UV-Vis absorption spectra of aqueous suspension of *S. cumini* CNCs, NC-1, NC-2 and NC-3.

Figure 6:
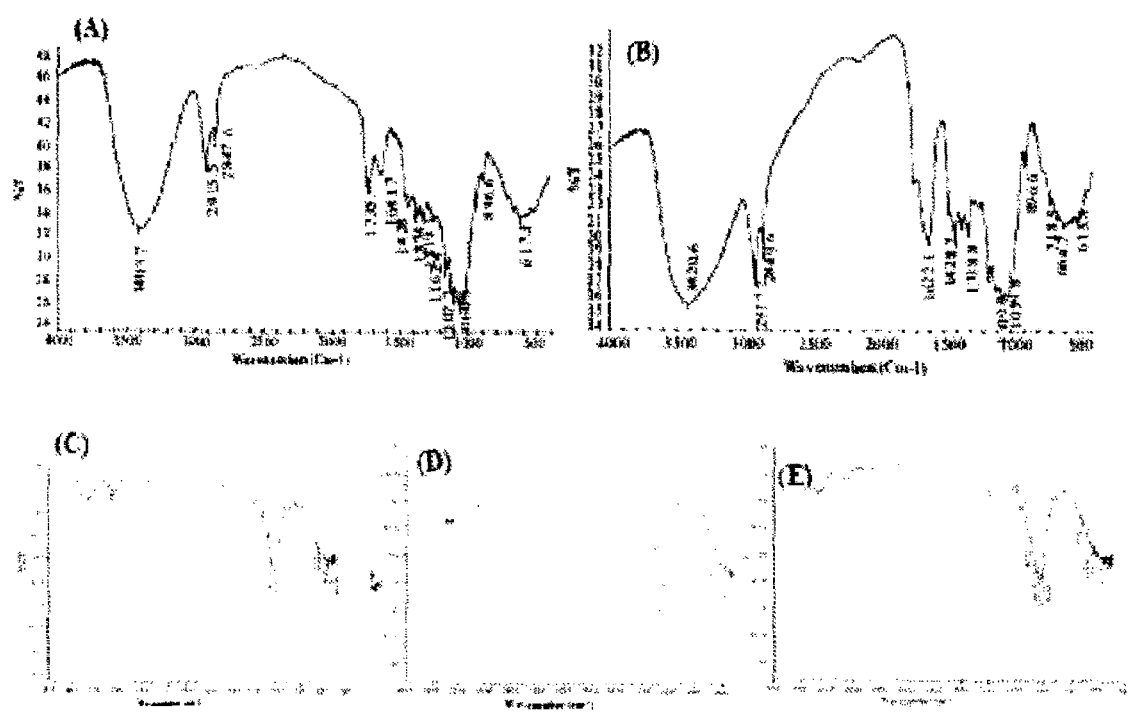

FIG. 6: Fourier transform infrared spectroscopy (FTIR) spectra of (A) untreated *S. cumini* leaf; (B) cellulose nanocrystals of *S. cumini*; (C) nanobiocomposite formed from CNCs and 1 mM silver nitrate; (D) nanobiocomposite formed from CNCs and 5 mM silver nitrate; and (E) nanobiocomposite formed from CNCs and 10 mM silver nitrate solution.

Figure 7:
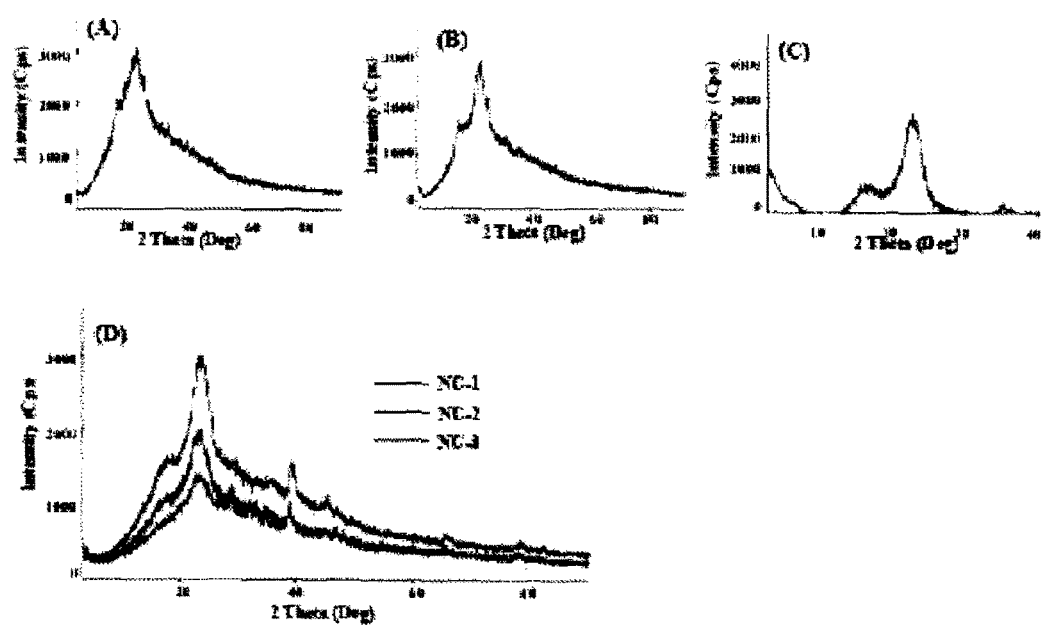

FIG. 7: X-ray powder diffraction (XRD) spectra of (A) untreated *S. cumini* leaf; (B) chemically pre-treated leaf fibers; (C) cellulose nanocrystals of *S. cumini*; (ID) overlay of XRD spectra of NC-1, NC-2 and NC-3.

Figure 8:
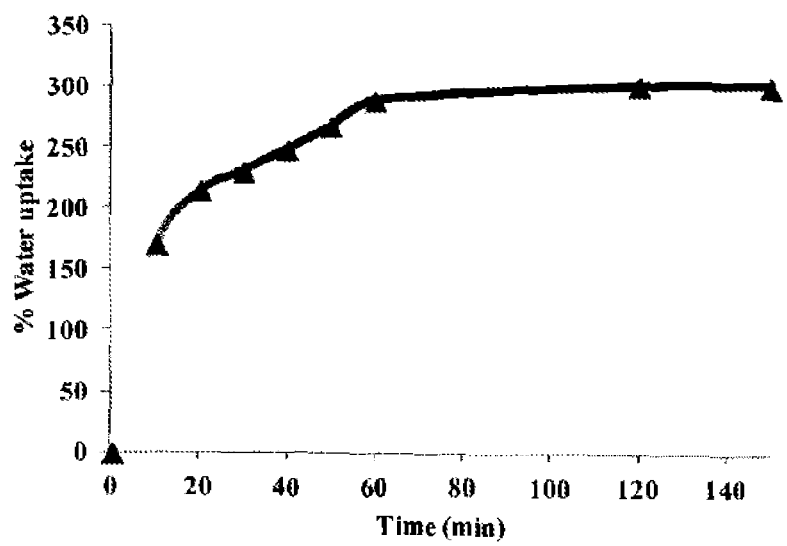

FIG. 8: Graph showing the water uptake capacity of *S. cumini* CNCs.

Figure 9:
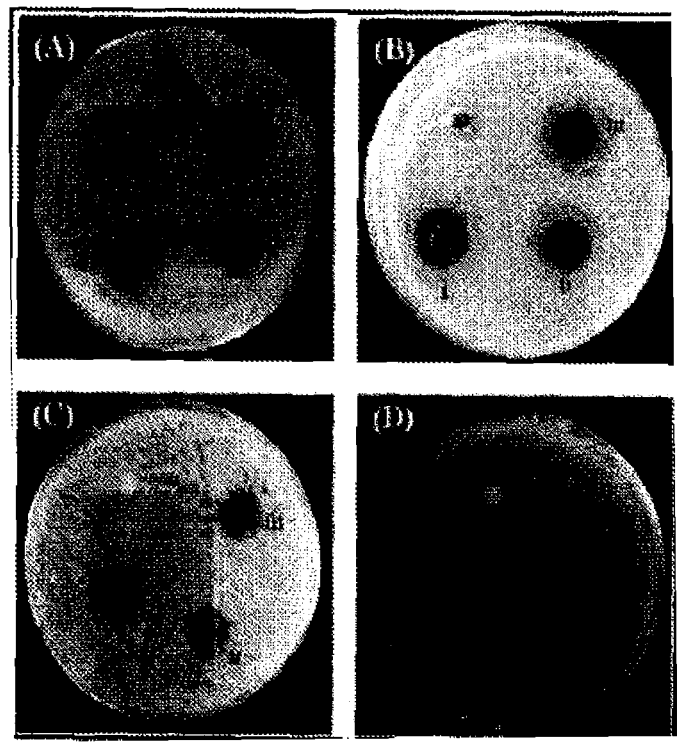

FIG. 9: Antimicrobial activity of nanobiocomposites NC-I, NC-2 and NC-3 ointments against (A) *E. coli*, (B) *B. subtilis*, by well diffusion method. The antibacterial activity of NC-1, NC-2 and NC-3 strip by disc diffusion method against (C) *E. coli*, (D) *B. subtilis*. The appearance of growth inhibition zone around NCs samples indicates the strong antimicrobial activity.

Figure 10:
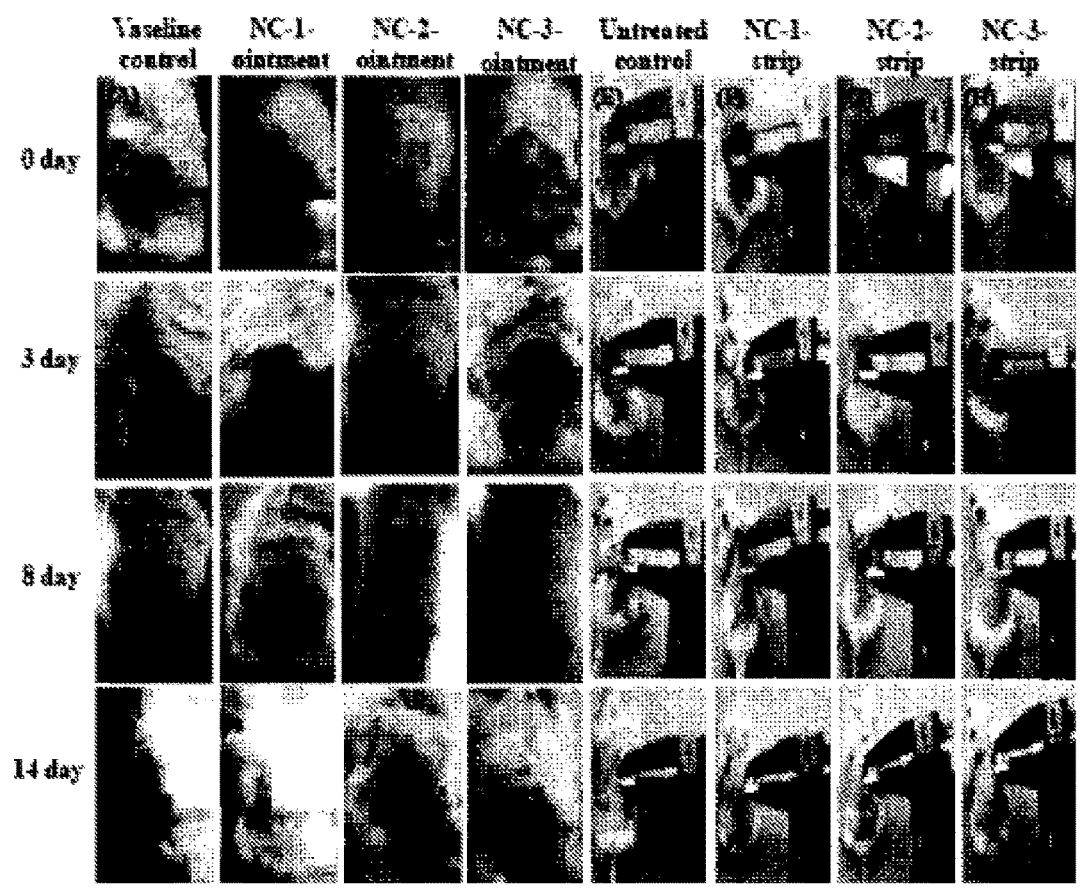

FIG. 10: Effects of NCs in ointments and strip forms on an in vivo wound healing mice model. Photographs show wounds treatment by (A) vaseline treated open wound (control); (B) NC-1-ointment; (C) NC-2-ointment; (D) NC-3-ointment; (E) untreated closed wound (control); (F) NC-1-strip; (G) NC-2-strip; and (H) NC-3-strip.

Figure 11:
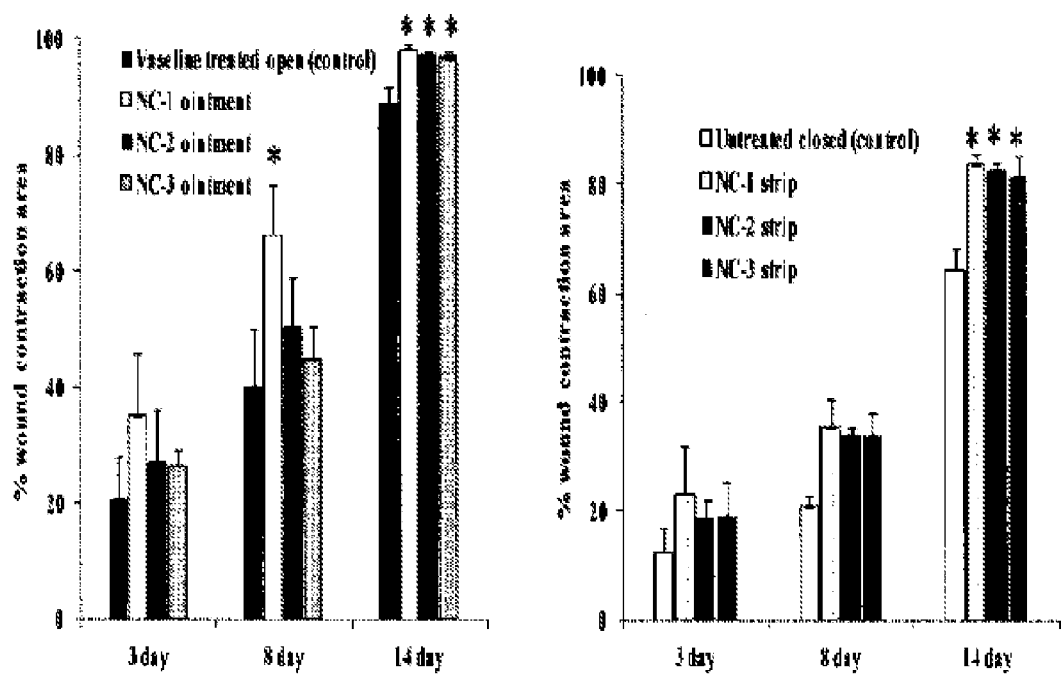

FIG. 11: The graph shows the % wound contraction area of each group of mice at day 3, 8 and 14 post wounding. The measurements are presented as mean±standard deviation, n=4 mice/group. Significant differences between the NCs treated and control groups are indicated by an asterisk mark, * ($p<0.05$).

Figure 12:
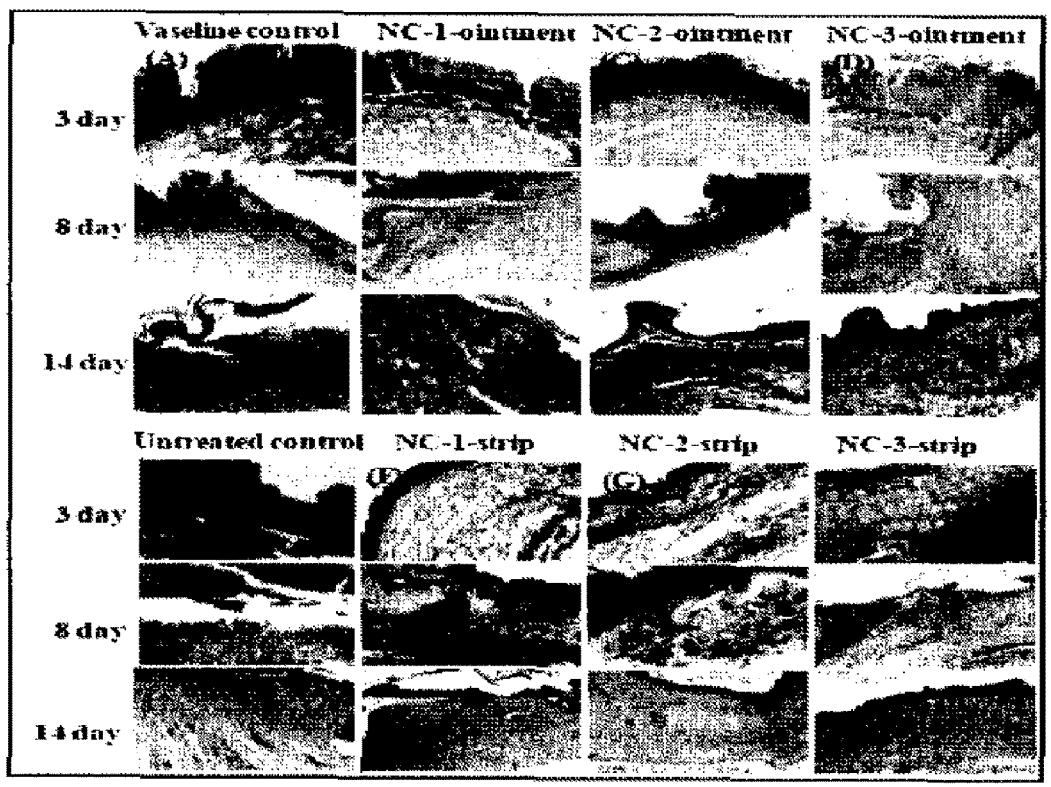

FIG. 12: H&E staining images of skin sections at day 3, 8 and 14 as seen under bright field microscope from (A) vaseline treated open wound (control); (B) NC-1-ointment; (C) NC-2-ointment; (D) NC-3-ointment; (E) untreated closed wound (control); (F) NC-1-strip; (G) NC-2-strip; and (H) NC-3-strip. The scale bars at the bottom of each image signify the size.

Figure 13:
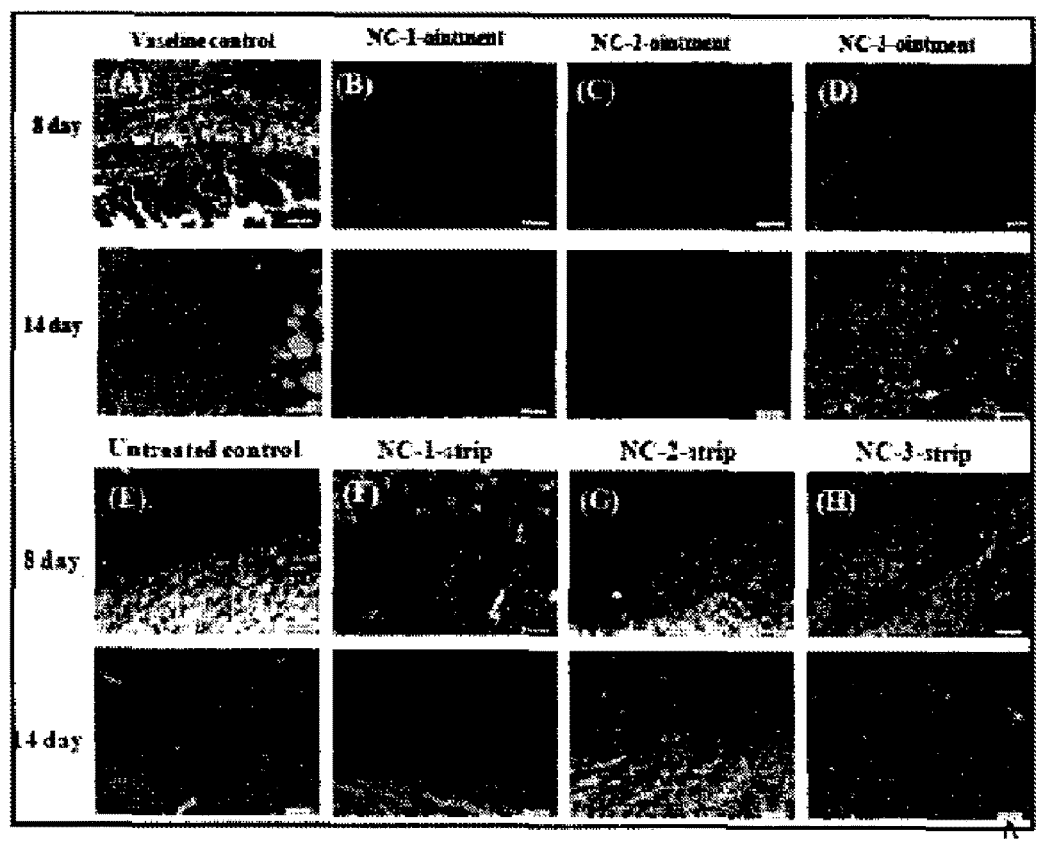

FIG. 13: Bright field microscopy images showing M&T staining slides of skin tissues of treated mice at day 8 and 14 (A) vaseline treated open wound (control); (B) NC-1-ointment; (C) NC-2-ointment; (D) NC-3-ointment; (E) untreated closed wound (control); (F) NC-I-strip; (G) NC-2-strip; and (H) NC-3-strip. The scale bar shows the magnification.

Figure 14:
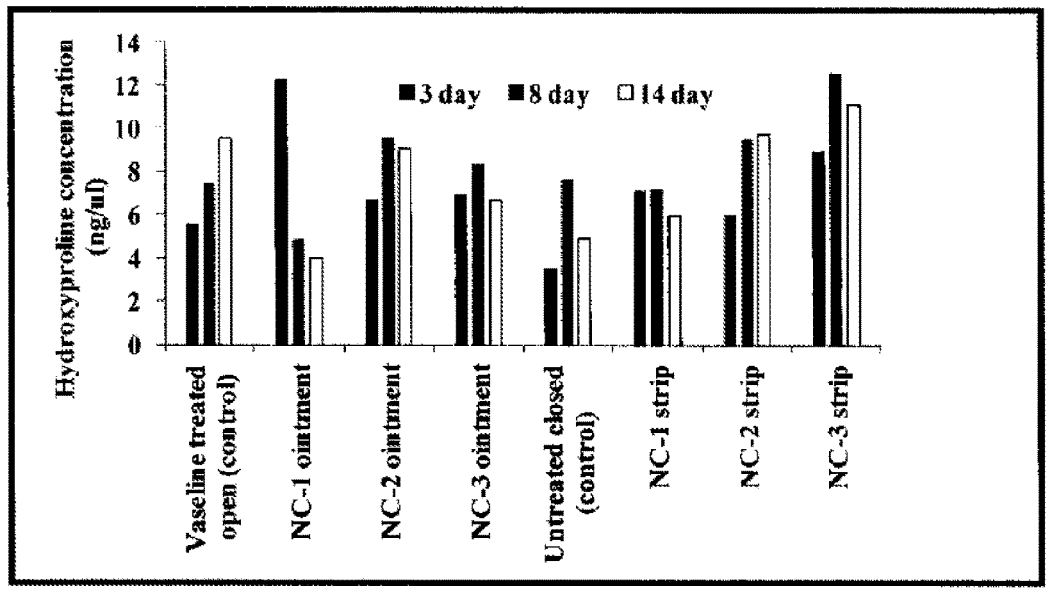

FIG. 14: Hydroxyproline content measured in serum samples of each group of mice at day 3, 8 and 14.

Figure 15:
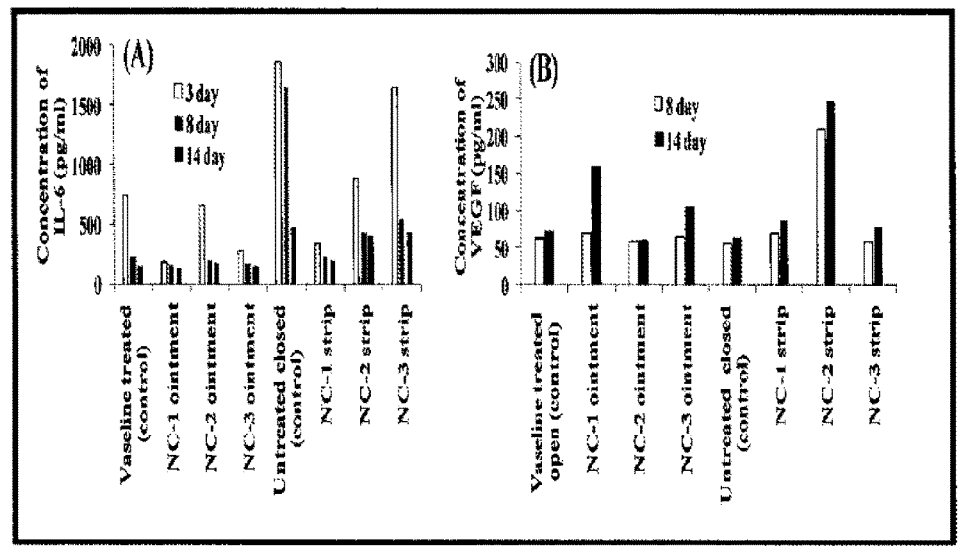

FIG. 15: Levels of IL-6 (A) and VEGF (B) in serum samples of each group of mice estimated through ELISA kits.

DETAILED DESCRIPTION OF THE INVENTION

Present invention relates to a nanobiocomposite formulation for wound healing and a process for the preparation thereof. The present invention describes a process for the isolation of cellulose nanocrystals from the plant leaves of *Syzygium cumini* by controlled and optimized chemomechanical treatment which has been found to be easy and inexpensive to manufacture. The invention encompasses the isolation and characterization of CNCs from the leaves of *Syzygium cumini*, formation of NCs comprised of CNCs as well as AgNPs. The use of developed NCs (ointment and strip) for antimicrobial and wound healing activities is also mentioned. Histopathology and serum biochemical assays were performed to study the effect of NCs on different phases of wound healing i.e. inflammation, proliferation and re-epithelization.

The isolation of CNCs from the leaves of *Syzygium cumini* is done using chemical method in combination with mechanical treatment. The use of *Syzygium cumini* leaves is preferred for the isolation of CNCs as the plant is large, evergreen, and perennial, widely distributed throughout and possesses medicinal values. *Syzygium cumini* leaves were collected from the plants grown in campus of CSIR-Institute of Himalayan Bioresource Technology (Council of Scientific & Industrial Research) Post Box No. 6, Palampur (H.P.) 176061-INDIA whose geographical origin is 32° 6' 39.0960" N, 76° 32' 10.5108" E and height above sea level is 1300 m. The examples of other plant biomass used for isolation of CNCs include, but not limited to, agricultural wastes of wheat, rice, soy-hulls, hemp, bamboo, banana, ramie etc. The chemical treatment with bleaching and alkali agents is followed by acid hydrolysis for the isolation purpose. Examples of appropriate bleaching agents include, but are not limited to, sodium chlorite, ammonium persulfate, and hydrogen peroxide. The preferred bleaching agent used in this invention is acidified sodium chlorite solution to remove the lignin present in plant leaf. Lignin is a chromophore present in the leaf. After that the alkali treatment involves the use of potassium hydroxide (KOH) to solubilize the pectins, hemicellulose present in the plant leaf. Other alkali agent like sodium hydroxide (NaOH) may be used. The removal of lignin, pectin and hemicelluloses present in plant is necessary to obtain the pure cellulosic fibers. All these treatments were given at high temperature of 80° C. for rapid solubilization of non-cellulosic impurities from the plant leaf. The high temperature range of 60-120° C. may be used. Time duration and concentration of chemical agents used also effect on the removal of non-cellulosic impurities. Alkali treatment was followed by acid hydrolysis. The type of acid used, concentration of acid used, reaction temperature and time duration of acid treatment affect the aspect ratio (length/diameter) of CNCs. In this invention, sulfuric acid ($H_2SO_4$) is preferably used as compared to hydrochloric acid, nitric acid and a mixture thereof, to reduce the length of fibers by breaking the amorphous regions present between crystalline regions of cellulose. Since the sulfuric acid impart negative charge to the fibers due to its sulfate ions, enhancing the fiber stability. The chemical treatment is followed by mechanical treatment of probe ultra-sonication to further individualize and reduce the size of the isolated CNCs. Time of sonication also affect the size of CNCs. CNCs after acid hydrolysis were sonicated for 4, 8, 12, 20 and 30 minutes to analyze its effect on size of CNCs. Further, 12 mM of sonication is preferred in this study to isolate CNCs of a particular length and diameter. Untreated leaf fibers, chemically pre-treated fibers and finally obtained CNCs are characterized by zeta potential measurements, SEM, TEM, FTIR, XRD and UV-Vis spectroscopy to estimate the size, shape, surface charge and other structural attributes.

The second aspect of the invention considers the preparation of plant based NCs composed of *S cumini* CNCs and AgNPs formed by the reduction of silver nitrate solution (1 mM, 5 mM and 10 mM). Silver iodide, silver bromide, silver citrate, silver acetate and silver chloride may also be used as silver salts. Here, silver nitrate is used as a precursor and water as a solvent. *S. cumini* LE has been used as a biological reducing agent as well as stabilizer rather than the use of chemical reducing agents and chemical stabilizers to reduce silver nitrate solution. A number of chemical reducing agents like sodium citrate, ascorbate, sodium borohydride, ethylene glycol etc. can be used for the reduction of silver salt solution. The chemical stabilizers used to prevent AgNPs from aggregation include polyvinylpyrrolidone (PVP), polyethylene glycol (PEG), sodium dodecyl sulphate (SDS), starch, glucose and many more. The chemical reducing agents are costly and cause great harm to environment, and living beings. The reason behind the use of biological *S. cumini* LE as a reducing agent as well as stabilizing agent in this invention is their environmental friendly nature, non-toxic to mankind and animals, cost effectiveness. Moreover, *S. cumini* LE possesses some medicinal properties like anti-oxidant, anti-inflammatory and antimicrobial which may provide an advantageous benefit to developed NCs for wound healing. The invention provides a novel nanobiocomposite NC material that includes AgNPs in metallic form bound to plant nanocellulose, CNCs. The NCs have been prepared using in situ approach where *S. cumini* LE was added drop wise to the mixture of CNCs and silver nitrate solution. *S. cumini* LE contains some phytochemicals which are responsible for the green reduction of silver nitrate solution into AgNPs. The LE also acts as a co-stabilizer to provide stability to AgNPs. The hydroxyl groups present on the surface of CNCs also assist in reducing silver nitrate solution. CNCs matrix itself acts as a biotemplate to limit the distribution of formed AgNPs. The present invention also describes that NCs have been prepared in two forms of wound dressing that include strip and ointment form. The composition of plant based nanocellulose present in the dressing can vary depending upon the method of preparation and the ultimate use of the wound dressing. The ability of NCs to be shaped into any desirable form gives the applicability of an added technology advantage. To make use of NCs in the form of an ointment, the inventors felt the need of addition of an inert base to NCs so to make it easy to apply on the body surface. A variety of inert and non-toxic bases (surfactants) are available in the pharmaceutical market like PEG, sorbitol, glycerin, petrolatum, chitosan and a mixture thereof But the present invention preferably deals with the use of Vaseline (petrolatum) as a cheap, inert and non-toxic ointment base to be added to NCs. NCs in the form of strip were prepared by casting the aqueous suspension of NCs in a mold of desirable size and shape, allowed it to dry at temperature range of 25-40° C., preferably 35° C. The plant cellulose fibers could be dried or never dried even after the incorporation of metallic silver NPs.

The developed NCs of plant nanocellulose functionalized with nanosilver exhibit a long lasting and broad spectrum antibacterial activity against a gram negative bacterium, *Escherichia coli* and gram positive bacterium, *Bacillus subtilis* selected from a group of bacteria. As these two bacteria are commonly found around and may cause an infection to wound. The bacterial growth inhibition around NCs is attributed to the diffusion of AgNPs from NCs material to the surroundings leading to the dampening of bacterial growth. The antimicrobial activity is derived from the component of metallic silver analogous to ionic silver. The use of nanocrystalline silver is advantageous over the use of conventional antibiotics due to the reason that silver as an antibacterial does not induce resistance in the microorganisms. The smaller size and larger surface area of nanosilver particles even enhance its bactericidal activity. The different sized and shaped AgNPs present in NC-1, NC-2 and NC-3 affect the bactericidal activity to a great extent. The exact mechanism behind bacterial inhibition is still unclear and subjected as a matter of extensive future research.

The other inventive step of the present invention where inventors have disclosed the topical use of all the three different formulations of plant based NCs in both the forms of strip as well as ointment, for acute wound healing in swiss albino mice model. The wound dressing product of present invention can also be used in disinfecting and treating patients with burns and scald related skin infection, incision cuts, wounds related to skin infection, surgery cut infections, vaginitis, chronic wounds, and diabetic ulcers.

The wound dressing of the present invention have moisture absorption capacity and can regulate the wound exudates. This means that a wound which is exudating can be topically treated by application of nanobiocomposite wound dressing of the present invention which will absorb excess fluid from the wound. The incorporated AgNPs inside CNCs matrix manifest antibacterial activity which is responsible for bacterial growth inhibition around the wound site. The duration of healing is variable and depends upon several factors that include the type of wound (closed or open, acute or chronic, incision or excision), cause and size of wound, age and nutritional status of patient. NCs of present invention are found to be safe, non-toxic and suitable for topical use in wound healing.

The present wound dressing materials in both the ointment as well as strip forms showed healing of wound in swiss albino mice model in a shortest possible time as compared to control untreated mice groups. The wound care product of present invention achieved wound healing by reducing inflammation, increasing angiogenesis, increasing proliferation, minimizing scarring, rapid and early collagen development, enhanced rate of wound closure and ultimately faster and more re-epithelization as observed from histopathology and biochemical serum estimations of treated mice. The wound dressing is biodegradable, biocompatible, and easily removed from wound site without any damage and pain to wounded skin.

Since plant based CNCs possess water uptake capacity, these can be used as efficient wound dressing material. The presence of moisture helps in activation of certain growth factors required for wound healing. There is a chance of minimal risk associated with bacterial infection due to moisture at wound site. To overcome the risk and provide the antibacterial activity, green AgNPs have been incorporated into CNCs matrix. The NCs prepared in this invention behave as suitable candidate for wound healing because they have the dual property of water uptake as well as antibacterial. The NCs can be molded in any desirable shape (ointment and strip) according to its applicability. The three different formulations of NCs (strip as well as ointment) have been prepared which will also help to further study the effect of concentration of silver nitrate solution used on the size of AgNPs formed and further effect on the antibacterial activity and wound healing potential. The efficacy of same NCs material in two forms of strip and ointment for wound healing potential in closed and open wound has also been described. The developed NCs show strong antimicrobial activity against both the gram negative and gram positive bacteria. NCs as wound dressing accelerate the wound healing by balancing the moisture content surrounding the wound site.

EXAMPLES

The following examples are given by way of illustration and should not be construed to limit the scope of the invention.

Example 1

Chemical Pre-Treatment of *S. cumini* Leaf for the Isolation of CNCs

Washed, air dried and small fragmented *S. cumini* leaves (4 g) treated with 50 ml of bleaching agent i.e. 3 wt % sodium chlorite solution (01=3.5) for 3 h at 80° C. The fibrous material was filtered and washed with distilled water and again treated with acidified 3% sodium chlorite solution (pH=3.5) at room temperature of 25±2° C. overnight (16-18 h) under stirring. Washing step was repeated as above. The material was then put into each of 3% KOH and 5% KOH for 2 h each at 80° C. under stirring. Again the fibrous material was treated with 3% sodium chlorite solution for 1 h at 80° C. Filtration and washing procedure was repeated after every treatment. The fiber at this stage was designated as chemically treated fiber.

The fiber at this stage was characterized for size and shape by SEM imaging. The chemical functional groups present in the untreated fiber were determined by FT-1R spectroscopy. To measure the crystallinity index, XRD analysis was carried out. SEM micrographs illustrated that chemically treated fibers were smooth with reduced in diameter as compared to bundles of untreated leaf fibers. FTIR spectra of chemically treated fibers showed that the peaks corresponding to lignin, pectin and hemicelluloses were removed during chemical treatment whereas these peaks were present in FTIR spectra of untreated leaf fibers.

Example 2

Isolation of CNCs by Acid Hydrolysis and Mechanical Treatment

The chemically pre-treated fiber was treated with 65% (v/v) sulfuric acid (1:9) for 1 h at 45° C. under constant stirring. The material was centrifuged and dialyzed against tap water to remove the acid content until neutral. The fibers at this stage were regarded as cellulose nanocrystals, CNCs. After chemical treatment, CNCs were given mechanical treatment using ultra probe sonication for 4, 8, 12, 20 and 30 min to individualize the fibers and to study the effect of sonication on the length of fibers. CNCs obtained were characterized and freeze dried to obtain white solid CNCs.

Example 3

Characterization of CNCs Using TEM, XRD, FT-IR, and Zeta Potential

CNCs were observed for shape and size estimation using TEM. The sample was mounted on copper grid, stained with uranyl acetate (3 wt %) and then washed with distilled water. The grid containing sample was allowed to air dry. Then the images were captured at desired magnification.

X-ray diffraction analysis was carried out to calculate the crystallinity index of nanocellulose. FT-1R analysis was done by forming the sample pellet with dry K13r. The spectrum was recorded at transmission of 4000-400 cm-1 to assure the presence of chemical functional groups that define the structure of cellulose.

Zeta potential measurements were carried out in disposable cuvettes on Zeta sizer Nano ZS to examine the surface charge on CNCs.

Example 4

Preparation of *S. cumini* Leaf Extract

Properly washed, finely chopped *S. cumini* leaves (4 g) were put into 50 ml of distilled water and kept overnight at room temperature. Then material was filtered through a mesh, filtrate was referred as LE and stored at 4° C. for further use as a biological reducing agent.

Example 5

Preparation of NCs

NCs containing CNCs and incorporated AgNPs were prepared by the adoption of in situ approach. For this purpose, 100 mg freeze dried CNCs (1 wt %) were added to 10 ml each of 1 mM, 5 mM and 10 mM silver nitrate solution and sonicated for 2 min. Then 1 ml (10% v/v) of *S. cumini* LE was added drop wise to each of the mixture and kept under stirring conditions for 6 h at room temperature. *S. cumini* LE caused the reduction of silver nitrate solution into AgNPs and stabilized them. Even the hydroxyl groups present on the surface of CNCs act to reduce the silver nitrate and control the size distribution of AgNPs. After that, the mixture was centrifuged, supernatant was discarded. The pellet was retained and referred as nanobiocomposite (NCs). The pellet of each of the three formulations of NCs was dissolved in distilled water and referred as NC-1, NC-2 and NC-3 prepared by the initial use of 1 mM, 5 mM and 10 mM silver nitrate solution, respectively.

Example 6

Development of Ointment and Film Forms of NCs

The NCs pellet of each of the mixture was dissolved separately in distilled water, and vortexed properly. The aqueous suspension of each of NC-1, NC-2 and NC-3 was casted into a mold and allowed to oven dry in the form of NCs strip. To be used as an ointment, the pellet of each of NC-1, NC-2 and NC-3 was directly mixed with Vaseline (petroleum jelly) used as an inert and non-toxic base in the ratio of 1:1. The six final products obtained were designated as NC-I-strip, NC-2-strip, NC-3-strip, NC-I-ointment, NC-2-ointment, and NC-3-ointment.

Example 7

Characterization of Nanobiocomposites (NCs)

UV-Vis spectrum was recorded for various forms of NCs at wavelength around 300-800 nm. 1 ml of diluted aqueous suspension was put into quartz cuvette and spectrum was recorded. The distilled water was taken as blank. The aqueous suspension of CNCs was taken as a reference.

Zeta potential was recorded to know the surface charge on each sample surface. For this, 1 ml of aqueous suspension of sample was put in the disposable zeta potential cuvette and then recorded the surface charge.

The aqueous suspension of each of the three NCs was characterized for shape and size using TEM. The sample was mounted on copper grid, washed with distilled water. The grid containing sample was allowed to air dry. Then the images were captured by TEM at desired magnification. XRD was done to confirm the presence of AgNPs incorporated in CNCs matrix for each of NC-1, NC-2 and NC-3.

FT-1R was done by forming the sample pellet with dry KBr. The spectrum was recorded at transmission of 4000-400 $cm^{-1}$.

Example 8

Determination of Water Uptake Capacity of CNCs Film

The initial weight of CNCs membrane was recorded. The pre-dried CNCs film was immersed in a vessel containing distilled water. Then the film was removed from the water at different time intervals to calculate the water uptake capacity until the constant weight was obtained. Final weight of the film was noted down.

Example 9

Antimicrobial Activity of NCs

All the three NCs, NC-1-strip, NC-2-strip and NC-3-strip were evaluated for antimicrobial activity against *E. coli* BL-21 strain and *B. subtilis* using disc diffusion method. The circular disc of NCs strip was placed on the microbial culture seeded agar plates (10 8 CFU/ml) and incubated for 24 h in an incubator at 37° C. The other three forms of NC-1-ointment, NC-2-ointment and NC-3-ointment were evaluated for antimicrobial activity by well diffusion method against *E. coli* BL-21 strain and *B. subtilis*. The growth inhibition zone was measured around the samples to investigate the antibacterial activity of NCs. CNCs were used as control in all cases.

Example 10

In Vivo Wound Healing Study of NCs

The wound healing potential of each of the developed NCs was evaluated in swiss albino mice model. The mice of age 6-8 weeks having 30-35 g body weight were categorized into eight groups (n=6 mice/group) according to the treatment. The mice were anaesthetized using an intraperitoneal injection of a mixture of xylazine and ketamine. The dorsal surface of mice was sterilized using 5% povidone/iodine solution. The circular full thickness skin wound of diameter 8 mm was created on the dorsal surface. The mice groups were given topical treatment of NCs strips as well as ointment accordingly. Group 1=Vaseline treated open wound (control), Group 2=NC-1-ointment, Group 3=NC-2-ointment, Group 4=NC-3-ointment, Group 5=Untreated closed wound (control), Group 6=NC-1-strip, Group 7=NC-2-strip, Group 8=NC-3-strip. The wound of mice was treated topically with each of ointment sample daily (50 mg/day/wound). The NCs strips were covered around the wound using adhesive tape. The dressing was changed every third day. The control open wound of mice was treated with sterilized vaseline daily whereas the wound of untreated closed group was wrapped with surgical gauze only. The % wound contraction area of wounded skin of each group of mice was measured on day 3, 8 and 14. Then mice of each group were euthanized on day 3, 8 and 14 to analyze the wound healing events occurring in skin tissue. The skin tissues of mice were taken for histopathology analysis.

Example 11

Histopathology of Skin of Mice to Study Wound Healing Mechanism

The skin tissues were dehydrated and cut sections of thickness 5 pm were stained with Haematoxylin and Eosin (H&E) staining protocol. The stained skin tissue sections (5 p.m) of mice of each treatment group at day 3, 8 and 14 were analyzed under bright field microscope for the histopathological observations. The cut skin tissue sections (5 pm) of each group of mice were also stained using Masson's Trichome procedure to analyze the collagen formation during wound healing at day 8 and 14.

Example 12

Estimation of Hydroxyproline, IL-6 and VEGF Content

The serum separated from the blood of each treated group of mice at day 3, 8 and 14 post wound was estimated for hydroxyproline, IL-6 and VEGF content through ELISA assay. The absorbance was noted at a particular wavelength to calculate the amount at these time intervals to study the effect of treatment of NCs as compared to control mice groups. The efficacy of the present invention can be compared as mentioned in table 1

TABLE 1

The measured % wound contraction area (mean + standard deviation) of each group of mice.

| Parameters | % wound contraction area (day 3) | % wound contraction area (day 8) | % wound contraction area (day 14) |
|---|---|---|---|
| Vaseline Control | 20.6 ± 7.21 | 39.9 ± 10.02 | 89.2 ± 2.67 |
| AgNPs only | 31.44 ± 5.07 | 62.5 ± 8.94 | 94.14 ± 2.34 |
| NC-1 (CNCs + AgNPs) ointment | 35.05 ± 10.94 | 66.3 ± 8.51 | 98.24 ± 0.75 |
| NC-2 ointment | 27.3 ± 8.90 | 50.39 ± 8.57 | 97.36 ± 0.58 |
| NC-3 ointment | 26.26 ± 3.04 | 44.92 ± 5.70 | 96.77 ± 1.12 |
| Untreated control (closed) | 12.44 ± 4.53 | 20.92 ± 1.96 | 64.56 ± 3.93 |
| NC-1 strip | 23.19 ± 8.87 | 35.43 ± 5.06 | 83.83 ± 1.93 |
| NC-2 strip | 18.65 ± 3.21 | 34.20 ± 0.97 | 83.03 ± 1.18 |
| NC-3 strip | 19.20 ± 6.18 | 33.89 ± 4.16 | 81.67 ± 3.49 |

Advantages of the Present Invention

The extractions of plant based CNCs are relatively easy and inexpensive as compared to microbial cellulose. Microbes are difficult to culture and maintain for few days, even sometimes the bacteria become resistant.

*S. cumini* LE also acts as a stabilizer to prevent aggregation of AgNPs. No additional chemical stabilizer was used in the present invention.

In situ approach is used for the development of NCs where CNCs act as biotemplate for controlling the size distribution of impregnated AgNPs. This approach involves the one pot synthesis for the reduction of silver nitrate solution into AgNPs as well as the impregnation of AgNPs inside CNCs matrix and imparts uniformity.

The present invention describes the in situ single vessel process of synthesis of AgNPs along with its simultaneous impregnation on CNCs matrix. In this process, Ag ions from AgNO3 solution were initially adsorbed onto CNCs surface by electrostatic or van der Waals forces and then reduced into AgNPs by using *S. cumini* leaf extract as biological reducing agent, expediting incorporation of AgNPs inside CNCs matrix to form NCs.

NCs wound dressing does not adhere to wound and is easily removed without causing any pain and damage to wound.

NCs promote wound healing by decreasing inflammation, increasing fibroblasts proliferation, early collagen formation, combating bacterial infection, fast reepithelization and tissue regeneration.

We claim:

1. A nanobiocomposite formulation (NCs) in ointment form comprising silver nanoparticles (AgNPs) and cellulose nanocrystals (CNCs) wherein the ratio of AgNPs and CNCs is in the range of 0.067%-0.4% w/w AgNPs: 7-8% w/w CNCs, and wherein the cellulose is derived from *Syzygium cumini* leaves.

2. A process for the preparation of the nanobiocomposite formulation in ointment form as claimed in claim 1, the method comprising:
   a) treating washed and dried *Syzygium cumini* leaves with bleaching agent at pH in the range of 3.0-4.0 for a time period ranging between 2-3 h at a temperature ranging between 70–100° C. to obtain a bleached fibrous material;
   b) filtering and washing the bleached fibrous material as obtained from (a) followed by treating with acidified bleaching agent solution at a temperature ranging between 22-30° C. for a time period ranging 16-18 h to obtain acidified fibrous material;
   c) washing the acidified fibrous material as obtained from (b) followed by keeping it in 2-18% base for 2 to 5 h at 70 to 80° C. under continuous stirring to obtain fibrous material;
   d) treating the fibrous material from (c) with 0.6 to 3% sodium chlorite solution for a time period ranging from 0.5 to 3 h at a temperature ranging from 80-100° C. followed by filtrating and washing to obtain a chemically treated fiber;
   e) treating the chemically treated fiber as obtained from (d) with 64-67% (v/v) acid in the ratio ranging from 1:5-1:9 for a time period ranging from 30-120 min at a temperature ranging from 40 to 80° C. under continuous stirring to obtain acidified chemically treated fiber;
   f) centrifuging and dialyzing the acidified chemically treated fiber as obtained from (e) against water to remove the acid content until neutral to obtain the CNCs;
   g) treating the CNCs as obtained from (f) mechanically for a time period ranging from 4-30 min to individualize the fibers and freeze drying to obtain white solid CNCs;
   h) dipping *Syzygium cumini* leaves in water for a period of time in the range of 20-28 h at a temperature in the range 20-30° C. followed by filtration and storing at a temperature 4-10° C. to obtain leaf extract as a biological reducing agent;
   i) freeze drying of the CNCs as obtained from (g) and adding each of 1 mM, 5 mM and 10 mM silver nitrate solution and sonicating for 2 to 5 min to obtain a mixture;
   j) adding 10-20% v/v of *Syzygium cumini* leaf extract as obtained from (h) to each of the mixture as obtained from (i) under continuous stirring for a time period ranging from 4 to 8 h at a temperature in the range of 20-30° C.;
   k) centrifuging the mixture as obtained in (i) to obtain the nanobiocomposite formulation (NCs).

3. The process as claimed in claim 2, wherein the bleaching agent is selected from the group consisting of sodium chlorite, ammonium persulphate, and hydroxide peroxide.

4. The process as claimed in claim 2, wherein the acid is selected from the group consisting of sulphuric acid, nitric acid, hydrochloric acid, and a mixture thereof.

5. The process as claimed in claim 2, wherein the base is selected from the group consisting of potassium hydroxide and sodium hydroxide.

6. The process for the preparation of the nanobiocomposite formulation as claimed in claim 2, wherein a pellet of the NCs is directly mixed with petrolatum base in the ratio of 1:1 to obtain the ointment form.

7. A process for treating a wound in a subject in need thereof, the process comprising topically applying the NCs of claim 1 to the wound.

8. The process of claim 7, wherein the wound is exudating.

* * * * *